United States Patent
Valleggi et al.

(10) Patent No.: US 8,312,764 B2
(45) Date of Patent: Nov. 20, 2012

(54) APPARATUS FOR DETECTING MECHANICAL FEATURES OF MATERIALS

(75) Inventors: Renzo Valleggi, Pontedera (IT); Luca Bosio, Pisa (IT)

(73) Assignee: S.M. Scienzia Machinale S.R.L., Navacchio (IT)

( * ) Notice: Subject to any disclaimer, the term of this patent is extended or adjusted under 35 U.S.C. 154(b) by 529 days.

(21) Appl. No.: 12/090,554

(22) PCT Filed: Oct. 17, 2006

(86) PCT No.: PCT/IB2006/002898
§ 371 (c)(1),
(2), (4) Date: Jun. 23, 2008

(87) PCT Pub. No.: WO2007/049111
PCT Pub. Date: May 3, 2007

(65) Prior Publication Data
US 2008/0282783 A1    Nov. 20, 2008

(30) Foreign Application Priority Data
Oct. 25, 2005   (IT) ................ PI2005A0117

(51) Int. Cl.
*G01N 3/42* (2006.01)
(52) U.S. Cl. .......................................... 73/82
(58) Field of Classification Search .......... None
See application file for complete search history.

(56) References Cited

U.S. PATENT DOCUMENTS

| | | | |
|---|---|---|---|
| 2,365,348 A | 12/1944 | Lyon et al. | |
| 3,102,417 A | 9/1963 | Chambers | |
| 4,036,048 A | 7/1977 | Webster | |
| 4,331,026 A * | 5/1982 | Howard et al. | 73/81 |
| 5,288,167 A * | 2/1994 | Gaffard et al. | 404/84.05 |
| 2003/0060987 A1* | 3/2003 | Dao et al. | 702/42 |

FOREIGN PATENT DOCUMENTS

| | | |
|---|---|---|
| GB | 626871 | 7/1949 |
| GB | 812514 | 4/1959 |
| GB | 936189 | 9/1963 |

* cited by examiner

*Primary Examiner* — Peter Macchiarolo
*Assistant Examiner* — Alex Devito
(74) *Attorney, Agent, or Firm* — Dennison, Schultz & MacDonald

(57) ABSTRACT

An apparatus (1) for detecting mechanical features of materials, in particular metal materials, comprising an indenter (10) adapted to be pushed against a sample material (15) in which it penetrates for a depth (h) and responsive to the hardness of the materials same. The apparatus (1) provides means for generating a measured force (F) and a transmission gear (35) which changes the rotational motion of shaft (40) of motor (30) into a linear reversible movement. The force generated is then amplified in a hydraulic way and transmitted to the indenter (10). This solution allows to lighten and to reduce the size of the mechanisms for generating the force, reducing also wear and mechanical backlash, as well as costs and overall dimensions. An advantage is also to measure with precision the stroke of the indenter with corresponding control in precision of the penetration (h) of the indenter in the sample material.

11 Claims, 4 Drawing Sheets

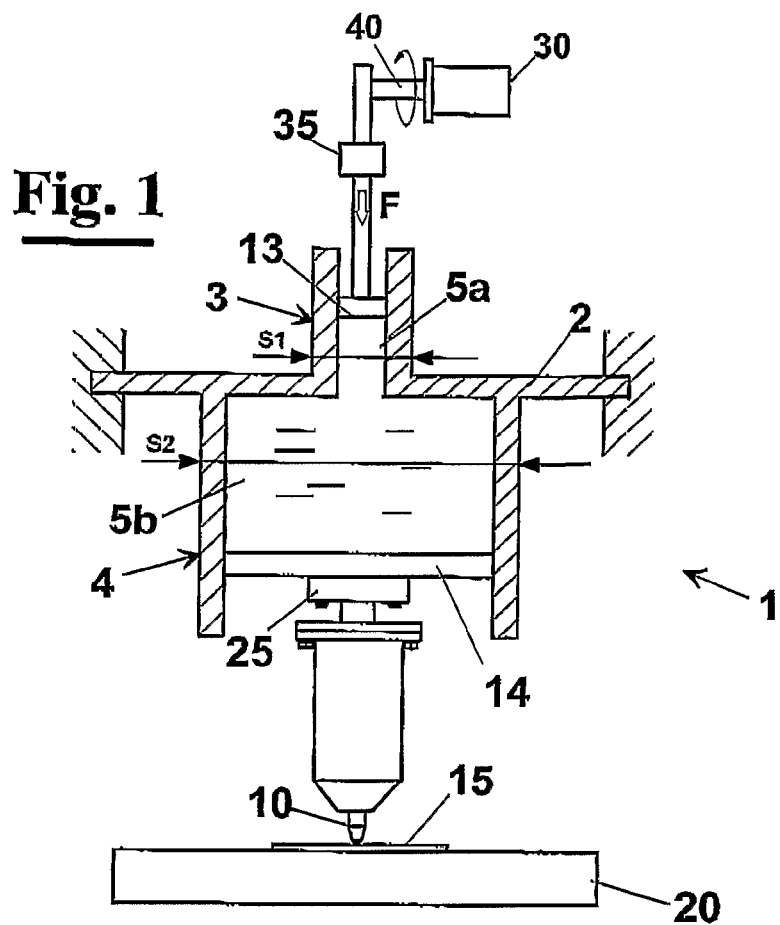
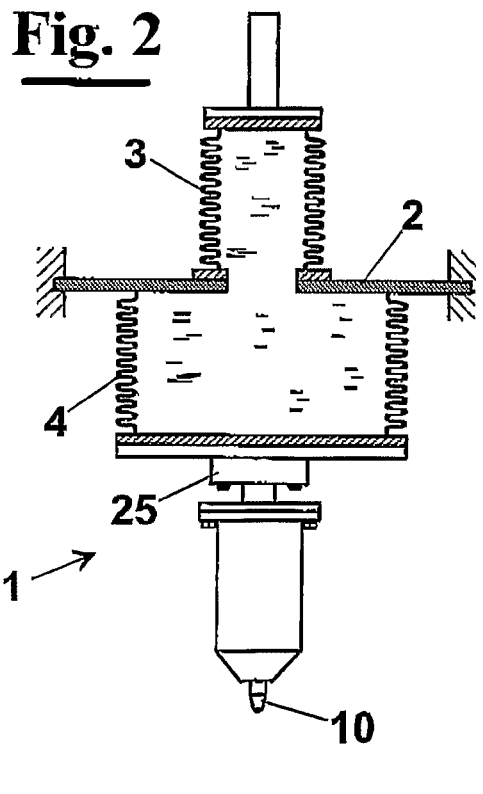
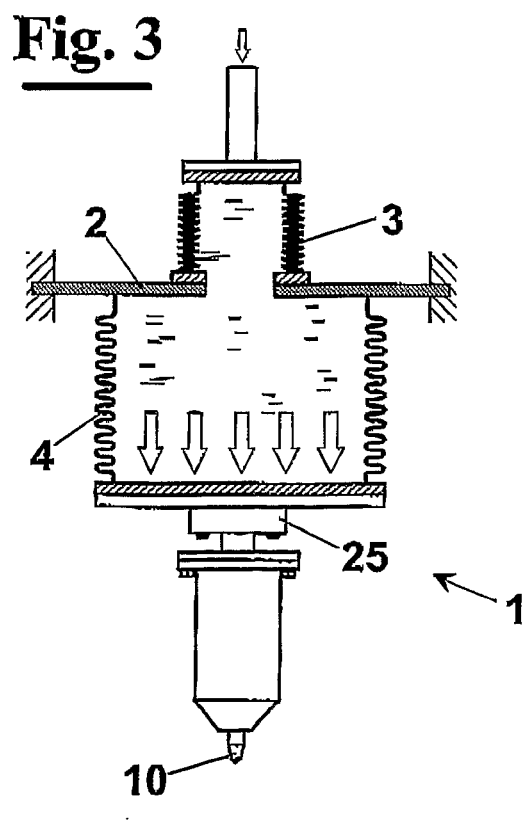

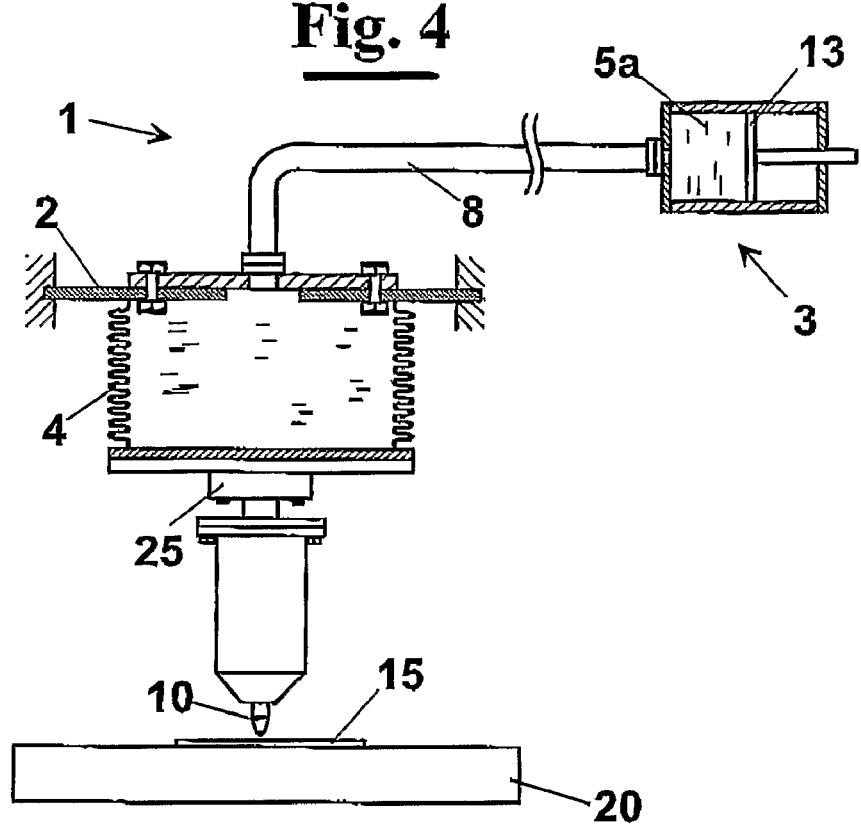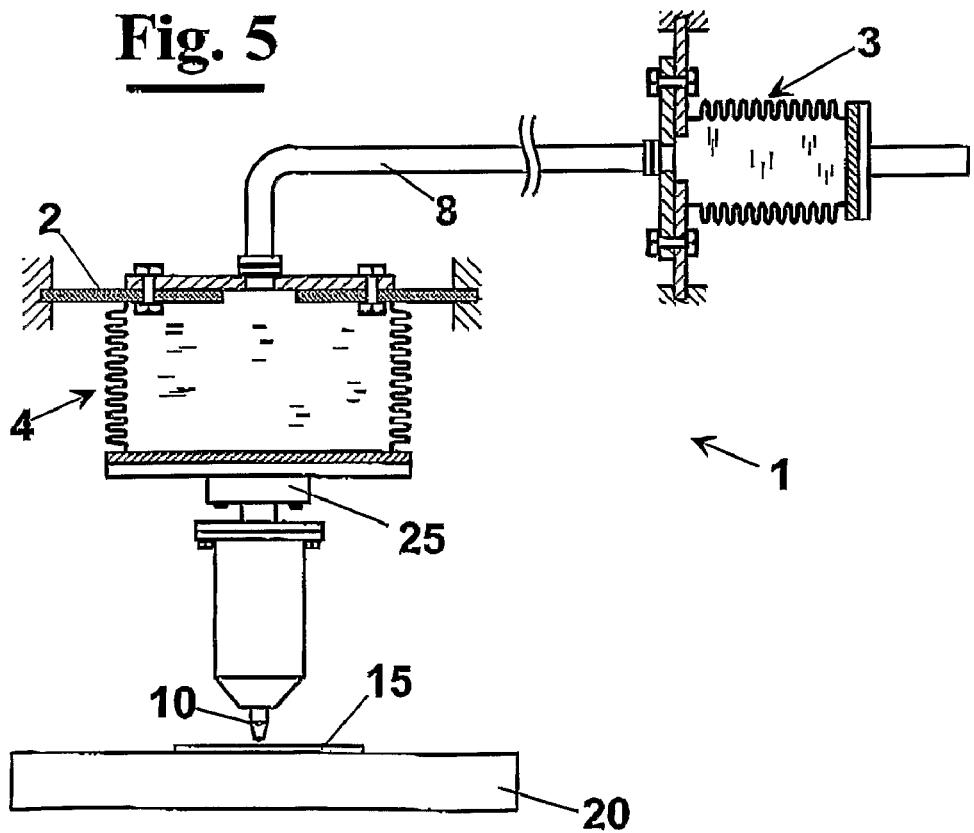

APPARATUS FOR DETECTING MECHANICAL FEATURES OF MATERIALS

FIELD OF THE INVENTION

The present invention relates to an apparatus for detecting mechanical features of materials, in particular metal material, which can be used for tests of indentation.

BACKGROUND OF THE INVENTION

As well known, for detecting mechanical features of a metal material, hardness tests exist that are executed on samples by an element having high hardness (indenter) that is pushed, with a controlled contact force P, against a surface of the sample for causing a permanent deformation on it.

For describing satisfactorily the mechanical features of a metal material, the following parameters are used: yield stress $\sigma_{sn}$, strain-hardening coefficient n and elastic modulus E. In fact, the strain-stress curve $\sigma$-$\epsilon$, which describes graphically the features of a metal material, is completely definable on the basis of such amount, for example according to the known Hollomon equation:

$$\sigma = \begin{cases} E \cdot \varepsilon & \varepsilon \leq \dfrac{\sigma_{sn}}{E} \\ \sigma_{sn}^{(1-n)} \cdot E^n \cdot \varepsilon^n & \varepsilon > \dfrac{\sigma_{sn}}{E} \end{cases}$$

In addition to the elastic modulus, which is a known starting parameter for a material or in any case a parameter obtainable with non-destructive tests, the other two parameters, i.e. the yield stress $\sigma_{sn}$ and the strain-hardening coefficient n, are obtained from the so called tensile test.

In known indentation apparatus, normally used for carrying out measurements of hardness of materials, the motion of the indenter towards the sample is effected, for example, by a step motor. The motor generates a force F that is amplified mechanically and then transmitted to the indenter through a suitable kinematical chain. The amplification of the force aims at a precise control on the stroke of the indenter and, in particular, on the depth of penetration h of the indenter in the material. This is possible, since, during the amplification, the force generated is multiplied for a fixed factor and at the same time the movement is reduced for the same factor. As above said, in the apparatus of prior art, the amplification of the force is obtained in a mechanical way, i.e. combining a reduction gear to the motor. The mechanical amplification allows then a precise measurement of the stroke h of the indenter and, however, it causes a high inertia and problems of mechanical wear.

Furthermore, to ensure to the apparatus a high centering precision during an indentation test, it is necessary to assemble the indenter on a structure having high structural stiffness, generally equipped with guides on which the indenter is mounted for driving it with respect to the tested sample. Therefore, the apparatus of prior art are structurally complex and have a high encumbrance.

SUMMARY OF THE INVENTION

It is therefore an aspect of the invention to provide an apparatus for detecting the mechanical features of materials, in particular metal materials, which carries out measurements on a tested sample with high precision.

It is another feature of the present invention to provide such an apparatus that is structurally easy, light and not much cumbersome.

It is also a feature of the present invention to provide such an apparatus for avoiding the drawbacks of the solutions of prior art.

These and other features are accomplished with one exemplary apparatus for detecting mechanical features of materials, in particular metal materials, according to the invention, the apparatus comprising:

- an indenter adapted to be pushed against a sample material and to penetrate in the material same for a depth correlable to its hardness;
- means for generating a measured force;
- means for amplifying the force produced by the means for generating and for applying it to the indenter;
- whose characteristic is that the means for amplifying the force are of hydraulic type.

Preferably, the means for amplifying the force comprises at least one hydraulic actuator.

In particular, the means for amplifying the force provides:

- a first hydraulic actuator, to which the force produced by the means for generating is applied;
- a second hydraulic actuator, in hydraulic connection with the first actuator, the second hydraulic actuator having a cross section larger than the first actuator and being operatively connected to the indenter to which it transmits the amplified force.

In an exemplary embodiment of the present invention, at least one among the first and the second hydraulic actuator is a bellows. This way, it is possible to reduce the loss of fluid of transmission that would leak if the hydraulic actuator were a piston slidingly mounted in a cylinder.

Preferably, the first and the second hydraulic actuator are two bellows in hydraulic connection arranged in series.

Advantageously, the apparatus comprises, furthermore:

- means for measuring in successive instants (t1, t2, t3, . . . ti, . . . tN) the instant values of the contact force P of the indenter on the sample;
- means for measuring the depth of penetration h of the indenter in the sample,
- means for analysing couples of data generated associating at each instant of detection the values of the contact force P with the relative values of penetration h.

In particular, the means for measuring the penetration h of the indenter in the sample provides at least one position sensor near the indenter. The arrangement of the position sensor near the indenter allows reducing possible linear deformation to which the apparatus is subject while detecting the data.

Preferably, the means for measuring the depth of penetration h of the indenter in the sample provides three position sensors that are not aligned and are arranged near the indenter same. The three position sensors, for example, can be arranged at 120° from one another along a circumference concentric to the indenter. By the three position sensors a measure is obtained relative to the plane defined by the three points where the three sensors are arranged. Therefore, the measurement is independent from the possible rotations that occur during the operation of the apparatus between the tested sample and the indenter thus obtaining measurements with high precision.

In particular, the position sensors can be selected from the group comprised of:
- inductive sensors;
- capacitive sensors;
- laser sensors, in particular, sensors of LVDT type (Linear Variable Differential Transformer).

Advantageously, the means for generating the force comprises a rotating element coupled to a translating element integral to actuator. More in detail, the force is generated by the rotation of the rotating element for a predetermined number of turns.

Preferably, the matching between the rotating element and the translating element is selected from the group comprised of:
- nut-screw;
- rack-pinion;
- ballscrew.

In particular, the means for analysing couples of data of force and penetration h can provide:
- correlation means adapted to execute a search and comparison step for selecting, among a plurality M of calculated curves defined as Pt1=ft(h), Pt2=ft(h) ... PtJ=ft(h) ... PtM=ft(h), which curve better approximates the experimentally measured values Psi,hsi, said correlation means being adapted to output a yield stress $\sigma_{sn}$ and a strain-hardening coefficient n associated to the selected curve and expressing the yield stress $\sigma_{sn}$ and the strain-hardening coefficient n of the material of the tested sample.

The apparatus above described can be, in particular, used for carrying out a method for detecting mechanical features of materials, in particular metal materials, comprising the following steps:
- prearranging an indenter adapted to penetrate in a sample of a material to analyse for a depth (h) measurable with a measurable force (P);
- creating a database comprising a finite number of reference curves (P,h) reproducing the course of the force applied (P) responsive to the depth of penetration (h), said database being built starting from values of yield stress ($\sigma_{sn}$) and strain-hardening coefficient (n) for a determined number of materials for which said values are known;
- running an indentation test on the sample to analyse by said indenter with detection and registration of values of force (P) and depth (h) at successive instants during the penetration of said instrument in the sample, obtaining a succession of couples of measured values (P,h) for each measuring instant;
- controlling the succession of couples of measured values (P,h) with selection from said database of at least one of said reference curves (P,h);
- displaying the values of the parameters of interest, in particular, strain-hardening coefficient (n) and yield stress ($\sigma_{sn}$), corresponding to said or each reference curves (P,h) thus extrapolated.

In particular, the above method is object of the patent application IT TO 2004A000535 in the name of the same applicant and that is here incorporated by reference.

BRIEF DESCRIPTION OF THE DRAWINGS

The invention will now be shown through the following description of an exemplary embodiment thereof, exemplifying but not limitative, with reference to the attached drawings wherein:

FIG. 1 shows diagrammatically a first exemplary embodiment of an apparatus for detecting mechanical features of materials, in particular metal materials, according to the invention;

FIGS. 2 and 3 show diagrammatically in two different operative steps an exemplary embodiment of the apparatus of FIG. 1;

FIGS. 4 to the 7 show diagrammatically further exemplary embodiments of the apparatus of FIG. 1, which illustrate the various elements;

DESCRIPTION OF A PREFERRED EXEMPLARY EMBODIMENT

Figure 6:
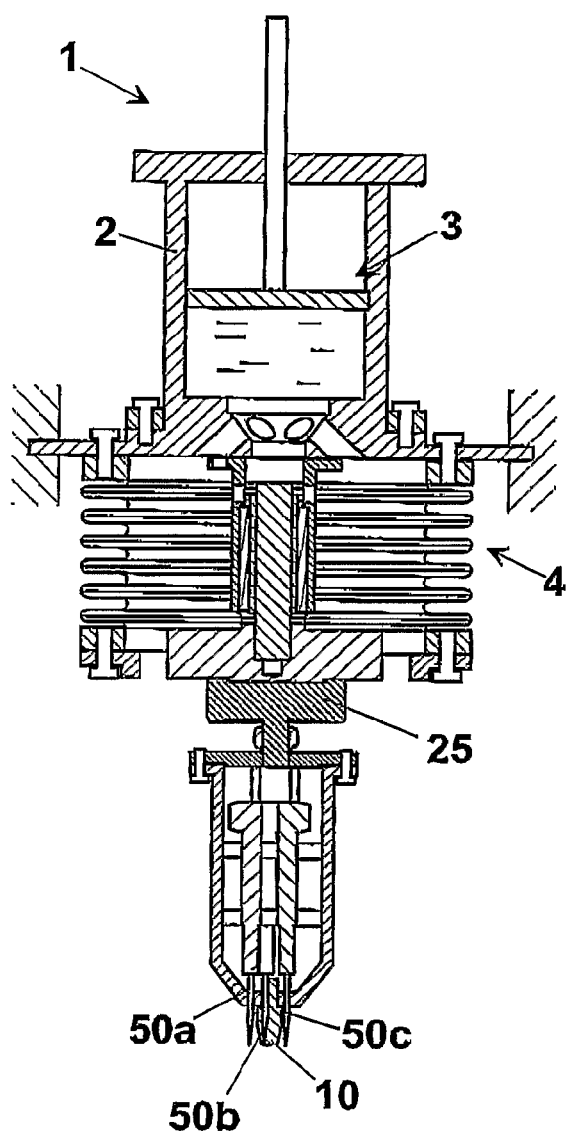

In FIG. 1 the operation is diagrammatically shown of an apparatus 1 for detecting mechanical features of materials, in particular metal materials, according to the invention. The apparatus 1 provides an indenter 10 adapted to be pushed against a sample material 15 in which it penetrates for a depth h not shown and responsive to the hardness of the materials same.

Apparatus 1 provides means for generating a measured force F, for example a step motor 30 (FIG. 8), and a transmission gear 35, for example a ballscrew (FIG. 7), which changes the rotational motion of shaft 40 of motor 30 into a linear reversible movement. The force generated by motor 30 is then amplified in a hydraulic way and transmitted to indenter 10. This is made by a first hydraulic actuator 3 comprising for example a piston 13 having a chamber 5a with a cross section S1 in hydraulic connection with a second hydraulic actuator 4 having a chamber 5b with a cross section S2, larger than S1, in which a piston 14 is arranged. The difference between the cross sections of chambers 5a and 5b and of bellows 13 and 14 carry out, as known, an amplification of the force generated F like that of a hydraulic press. The adoption of this solution for an indenter is particularly advantageous, because it allows to lighten and to reduce the size of the mechanisms for generating the force, reducing also wear and mechanical backlash, as well as costs and overall dimensions. An advantage is also to measure with precision the stroke of the indenter with corresponding control in precision of the penetration h of the indenter in the sample material.

In an alternative exemplary embodiment of the invention at least one hydraulic actuator 3, or 4 can be a bellows. In FIGS. 2 and 3 a case is shown where both the hydraulic actuators 3 and 4 are bellows. More in detail, bellows 3 and 4 are arranged in series and at their adjacent walls they are locked to a fixed frame, not shown in the figures, by a plate 2. In this case, a thrust on the fluid motor is exerted by the walls of bellows 3 and 4 during their alternated extension/shrinkage. Like the previous case, the amplification of force F is made owing to the difference between the cross sections of the two bellows 3 and 4. As shown in FIGS. 4 and 5, the first hydraulic actuator 3 can be arranged even at considerable distance with respect to the second actuator 4 to which it is hydraulically connected by a duct 8.

Figure 7:
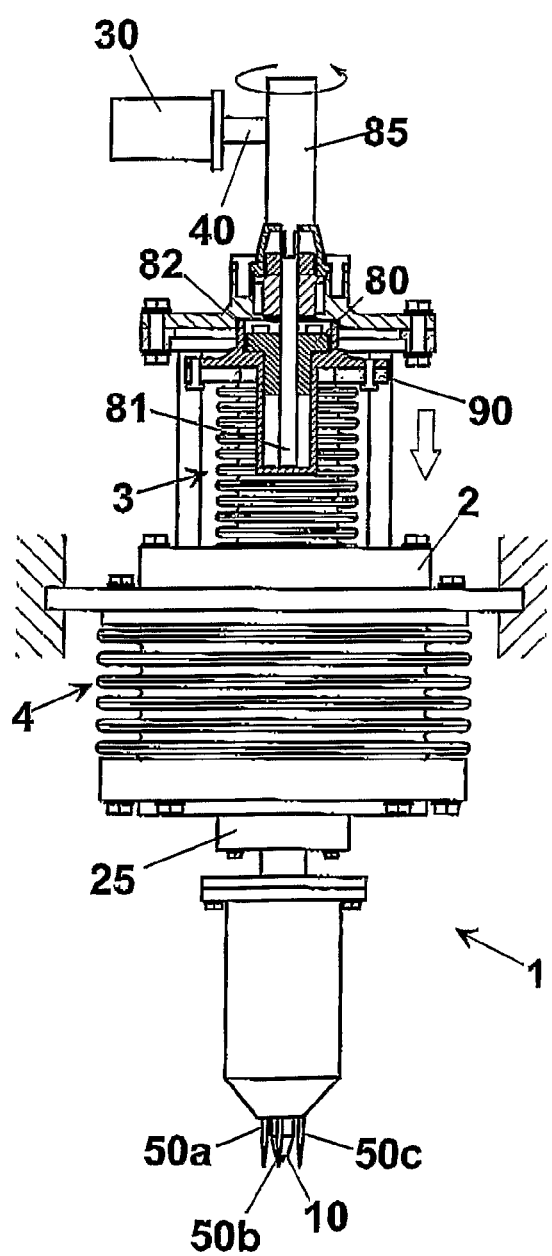
Figure 8:
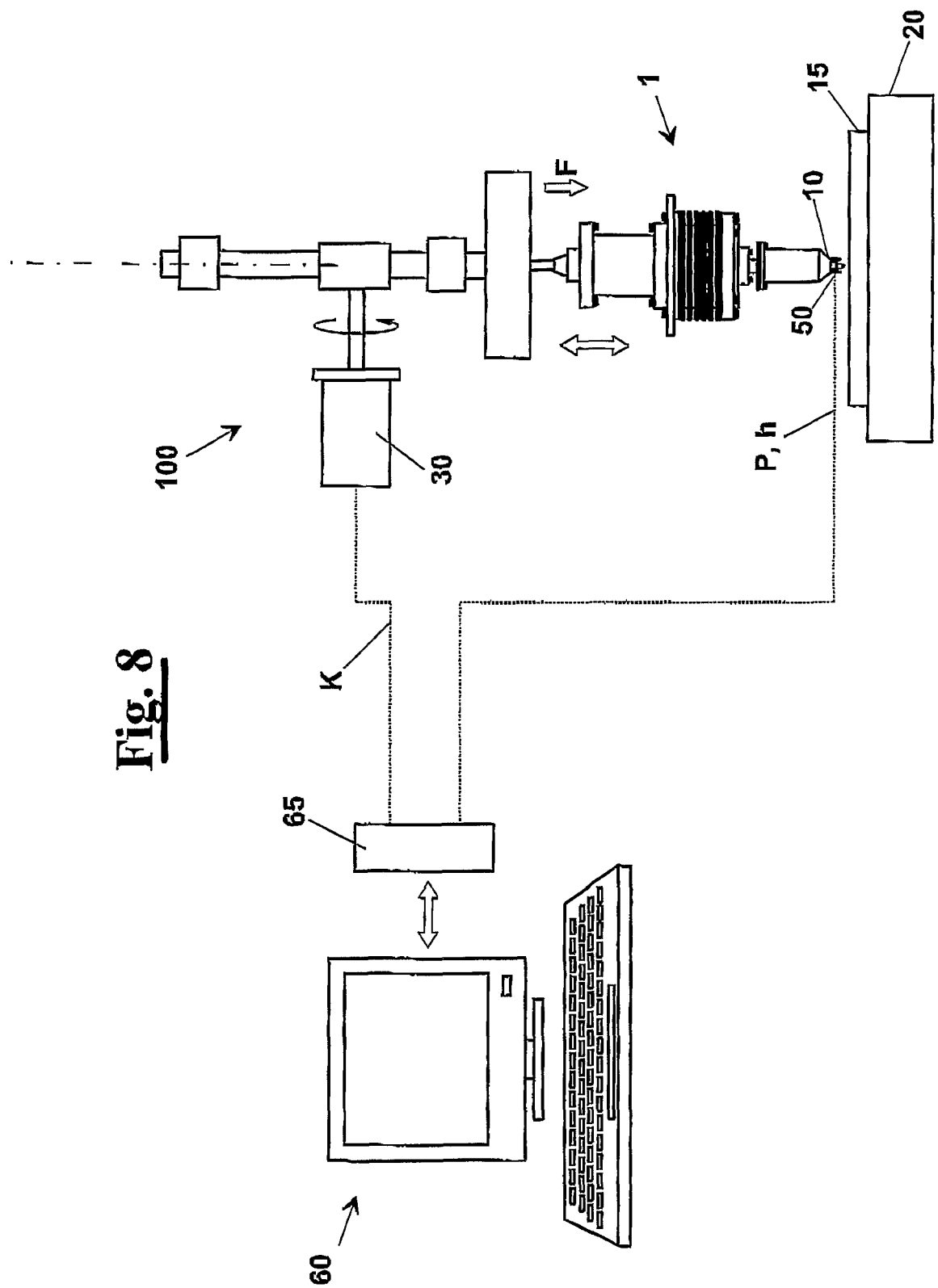
FIG. 8 shows diagrammatically a layout of a machine for detecting mechanical features of materials, which uses the apparatus of FIG. 1 for carrying out a measuring test.

As shown in FIG. 7, motor 30 is connected by a shank 85 to a ballscrew 81. The latter, during its rotation, causes a nut 80 to it coupled to translate. Translation of nut 80 causes then the operation of first hydraulic actuator 3.

Nut 80 is integral to a flange 90 that is the upper wall of bellows 3. This way, at each translating of nut 80 there bellows 3 shrinks and thrusts the hydraulic fluid from first bellows 3 to second bellows 4, which has larger cross section than the former. The difference between the cross sections of first bellows 3 and second bellows 4 produces a multiplication of the transmitted force that is felt as amplified by indenter 10. Force F produced by motor 30 is thus amplified in a hydraulic way before being applied to indenter 10. Indenter 10, for example with end a spherical indenter, exerts contact force P on a sample 15 being tested.

Indenter 10 approaches, reaches and then penetrates in sample 15 with a controlled fixed extremely low speed (a few mm/minute). The spherical indenter 10 is coupled to a force sensor 25 (of known type) that outputs an electric signal responsive to the contact force applied by indenter 10 to sample 15.

The apparatus 1 is, furthermore, equipped with position sensors, for example three sensors 50a, 50b and 50c, in particular, but not exclusively of the LVDT type (Linear Variable Differential Transformer), arranged near indenter 10 for measuring penetration value h. The arrangement of position sensors 50a-50c near indenter 10 allows to eliminate possible linear deformations. The choice of arranging the three position sensors 50a-50c at 120° from each other along a circumference concentric to indenter 10, allows instead to carry out the detection with respect to a plane defined by the three points where the three sensors are arranged. Therefore, the measurement is independent from the possible rotations that occur during the operation of the apparatus 1 between sample 15 and indenter 10 thus obtaining measurements with high precision.

The data relative to the force determined by the sensor of force 25 and the position of sample 15 with respect to indenter 10, i.e. the penetration h in the sample, are sent to an interface device 65 that transmits them to a personal computer 60 for calculations. In other words, owing to the contact between indenter 10 and sample 15, the program of data acquisition senses at predetermined successive instants the measured contact force P and penetration h.

In particular, the used method for analysis is object of patent application IT TO 2004A000535 in the name of the same applicant and here incorporated by reference.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. Apparatus for detecting yield stress $\sigma_{sn}$, strain-hardening coefficient n, elastic modulus E, and strain-stress curve $\sigma$-$\epsilon$ of metal materials, said apparatus comprising:
   an indenter constructed and arranged to be pushed against a sample of the material and to penetrate into the material to a penetration depth (h), and that can be correlated to material hardness;
   a means for generating a predetermined force (F);
   a means for amplifying the force (F) produced by said means for generating and for applying the force to said indenter to exert a corresponding contact force (P) on the sample, wherein said means for amplifying said force is of an hydraulic type;
   a means for measuring in successive instants (t1, t2, t3, ... ti, ... tN) the value of the contact force (P) of said indenter on the sample;
   a means for measuring the penetration depth (h) of said indenter into said sample to obtain a penetration value; and
   a means for analyzing couples of data, each of said couples generated by associating, for each instant of detection, a measured value of the contact force (P) with a relative measured penetration value;
   wherein said means for measuring said penetration depth (h) comprises at least one position sensor arranged close to said indenter so as to reduce possible linear deformation to which the apparatus is subject while detecting said penetration depth and said force;
   wherein said position sensor is arranged close to said indenter, and along a circumference concentric to said indenter.

2. Apparatus according to claim 1, wherein said means for amplifying said force comprises:
   a first hydraulic actuator, to which a force produced by said means for generating is applied;
   a second hydraulic actuator, in hydraulic connection with said first hydraulic actuator, said second hydraulic actuator having a cross section larger than said first hydraulic actuator and being operatively connected to said indenter for transmitting thereto the amplified force.

3. Apparatus according to claim 2, wherein at least one of said first and said second hydraulic actuators is a bellows.

4. Apparatus according to claim 2, wherein said first and said second hydraulic actuators are two bellows in hydraulic connection arranged in series.

5. Apparatus according to claim 4, wherein said means for analyzing the couples comprises:
   correlation means adapted to execute a search and comparison step for selecting, among a plurality M of calculated curves defined as Pt1=ft(h), Pt2=ft(h) ... PtJ=ft(h) ... PtM=ft(h), which curve better approximates the experimentally measured values Psi,hsi, said correlation means being adapted to output a value of yield stress $\sigma$sn and a strain-hardening coefficient n associated to the selected curve and expressing the yield stress $\sigma$sn and the strain-hardening coefficient n of the material of the tested sample.

6. Apparatus according to claim 1, wherein said means for measuring the depth of penetration h of said indenter in said sample comprises said three position sensors that are not aligned and are arranged near said indenter.

7. Apparatus according to claim 1, wherein said at least one position sensor is selected from the group consisting of inductive sensors, capacitive sensors, and laser sensors.

8. Apparatus according to claim 2, wherein said means for generating comprises a rotating element coupled with a translating element integral to said first actuator, said force being generated by the rotation of said rotating element for a predetermined number of turns.

9. Apparatus according to claim 8, wherein said rotating element and said translating element are coupled by a coupling means that is selected from the group consisting of a nut-screw, a rack-pinion, and a ballscrew.

10. Apparatus according to claim 1, wherein said position sensor elements are of the Linear Variable Differential Transformer (LVDT) type.

11. Apparatus for detecting yield stress $\sigma_{sn}$, strain-hardening coefficient n, elastic modulus E, and strain-stress curve $\sigma$-$\epsilon$ of metal materials, said apparatus comprising:

an indenter constructed and arranged to be pushed against a sample of the material and to penetrate into the material to a penetration depth (h), and that can be correlated to material hardness;

a means for generating a predetermined force (F);

a means for amplifying the force (F) produced by said means for generating and for applying the force to said indenter to exert a corresponding contact force (P) on the sample, wherein said means for amplifying said force is of hydraulic type;

a means for measuring in successive instants (t1, t2, t3, . . . ti, . . . tN) the value of the contact force (P) of said indenter on the sample;

a means for measuring the penetration depth (h) of said indenter into said sample to obtain a penetration value; and a means for analyzing couples of data, each of said couples generated by associating, for each instant of detection, a measured value of the contact force (P) with a relative measured penetration value;

wherein said means for measuring said penetration depth (h) comprises at least one position sensor arranged close to said indenter so as to reduce possible linear deformation to which the apparatus is subject while detecting said penetration depth and said force;

wherein said position sensor comprises three position sensor elements arranged in a circumference concentric to said indenter, in order to carry out a detection operation by said indenter in a plane defined by three points where said three sensor elements are arranged.

* * * * *